(12) United States Patent
Buchanan et al.

(10) Patent No.: US 7,485,763 B2
(45) Date of Patent: Feb. 3, 2009

(54) USING A CATALYST HAVING TWO DIFFERENT ZEOLITES FOR TRANSALKYLATION OF A C9+ AROMATIC FEED

(75) Inventors: John Scott Buchanan, Lambertville, NJ (US); Ronald J. Cimini, Friendswood, TX (US); Robert A. Crane, Lumberton, TX (US); Wenyih F. Lai, Bridgewater, NJ (US); Jose G. Santiesteban, Baton Rouge, LA (US); David A. Stachelczyk, Houston, TX (US); David L. Stern, Annandale, NJ (US); Hye-Kyung C. Timken, Albany, CA (US); William A. Weber, Burlington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/592,832

(22) Filed: Nov. 3, 2006

(65) Prior Publication Data

US 2007/0055086 A1 Mar. 8, 2007

Related U.S. Application Data

(62) Division of application No. 10/294,428, filed on Nov. 14, 2002, now Pat. No. 7,148,391.

(51) Int. Cl.
*C07C 6/12* (2006.01)
(52) U.S. Cl. ..................................... 585/475
(58) Field of Classification Search .................. 585/475
See application file for complete search history.

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 3,766,093 A | 10/1973 | Chu | |
| 3,832,449 A | 8/1974 | Rosinski et al. | |
| 3,894,104 A | 7/1975 | Change et al. | |
| 4,016,218 A | 4/1977 | Haag et al. | |
| 4,016,245 A | 4/1977 | Plank et al. | |
| 4,076,842 A | 2/1978 | Plank et al. | |
| 4,083,886 A | 4/1978 | Michalko | |
| 4,333,854 A | 6/1982 | Antos | |
| 4,375,573 A | 3/1983 | Young | |
| 4,391,785 A | 7/1983 | Rosinski et al. | |
| 4,439,409 A | 3/1984 | Puppe et al. | |
| 4,452,769 A | 6/1984 | Chu et al. | |
| 4,537,758 A | 8/1985 | Chu et al. | |
| 4,539,193 A | 9/1985 | Valyocsik | |
| 4,552,738 A | 11/1985 | Rubin | |
| 4,552,739 A | 11/1985 | Kühl | |
| 4,585,637 A | 4/1986 | Rubin | |
| 4,585,746 A | 4/1986 | Valyocsik | |
| 4,698,217 A | 10/1987 | Valyocsik | |
| 4,783,568 A | 11/1988 | Schmidt | |
| 4,873,067 A | 10/1989 | Valyocsik et al. | |
| 4,954,325 A | 9/1990 | Rubin et al. | |
| 5,021,141 A | 6/1991 | Rubin | |
| 5,030,787 A | 7/1991 | Absil et al. | |
| 5,192,521 A | 3/1993 | Moini et al. | |
| 5,236,575 A | 8/1993 | Bennett et al. | |
| 5,250,277 A | 10/1993 | Kresge et al. | |
| 5,336,478 A | 8/1994 | Dwyer et al. | |
| 5,362,697 A | 11/1994 | Fung et al. | |
| 5,763,720 A * | 6/1998 | Buchanan et al. | 585/475 |
| 5,905,051 A | 5/1999 | Wu et al. | |
| 5,942,651 A | 8/1999 | Beech, Jr. et al. | |

FOREIGN PATENT DOCUMENTS

| | | |
|---|---|---|
| WO | WO97/45198 | 12/1997 |
| WO | WO 0038834 | 7/2000 |
| WO | WO 0208159 | 1/2002 |

OTHER PUBLICATIONS

"The Mathematics Of Diffusion", Oxford University Press, Ely House, London, 1967.
"Journal of Catalysis", vol. 4, p. 527 (1965).
"Journal of Catalysis", vol. 6, p. 278 (1966).
"Journal of Catalysis", vol. 61, p. 395.

\* cited by examiner

*Primary Examiner*—Thuan Dinh Dang
(74) *Attorney, Agent, or Firm*—Andrew B. Griffis

(57) ABSTRACT

In a process for converting $C_9+$ aromatic hydrocarbons to lighter aromatic products a feed comprising $C_9+$ aromatic hydrocarbons is contacted under transalkylation reaction conditions with a catalyst composition comprising (i) a first molecular sieve selected from the group consisting of ZSM-12, mordenite and a porous crystalline inorganic oxide material having an X-ray diffraction pattern including d-spacing maxima at $12.4\pm0.25$, $6.9\pm0.15$, $3.57\pm0.07$ and $3.42\pm0.07$; and (ii) a second molecular sieve having a constraint index ranging from 3 to 12. At least the first molecular sieve has a hydrogenation component associated therewith and the first and second molecular sieves are contained in the same catalyst bed. The $C_9+$ aromatic hydrocarbons are converted under the transalkylation reaction conditions to a reaction product containing xylene.

9 Claims, No Drawings

US 7,485,763 B2

USING A CATALYST HAVING TWO DIFFERENT ZEOLITES FOR TRANSALKYLATION OF A C9+ AROMATIC FEED

This application is a divisional application of Ser. No. 10/294,428, filed Nov. 14, 2002, now issued as U.S. Pat. No. 7,148,391, the disclosures of which are Incorporated by reference in their entireties.

FIELD

The invention relates to the conversion of heavy aromatics, specifically $C_9+$ aromatics, to lighter aromatic products, particularly benzene, toluene and xylene (BTX).

BACKGROUND

A source of benzene and xylene is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX, along with ethyl benzene.

Refineries have also focused on the production of benzene and xylene by transalkylation of C9+ aromatics and toluene over noble metal-containing zeolite catalysts. During the transalkylation of C9+ aromatics and toluene to high value petrochemical products, such as benzene and xylene, over catalysts containing noble metals, by-product saturated compounds are typically produced during the first several months on stream. These by-product saturated compounds can boil in the same temperature range as the desired aromatic products, making separation of the desired products at high purity levels difficult. For example, a benzene product for commercial sale must exceed 99.85% purity. However, initial benzene purity after distillation of a transalkylation reaction product is typically only 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

One solution to the problem of the production of benzene co-boilers during the transalkylation of heavy aromatics is disclosed in U.S. Pat. No. 5,942,651 and involves the steps of contacting a feed comprising $C_9$ + aromatic hydrocarbons and toluene under transalkylation reaction conditions with a first catalyst composition comprising a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. A benzene product having a purity of at least 99.85% may be obtained by distilling the benzene from the transalkylation reaction product, without the need for an additional extraction step. According to the '651 patent, the second catalyst composition comprises up to 20 wt % of the total weight of the first and second catalyst compositions.

U.S. Pat. No. 5,905,051 discloses a process for converting a hydrocarbon stream such as, for example, a $C_9$ + aromatic compound to $C_6$ to $C_8$ aromatic hydrocarbons, such as xylenes, by contacting the stream with a catalyst system comprising a first catalyst composition and a second catalyst composition, wherein said catalyst compositions are present in separate stages and are not physically mixed or blended and wherein said first catalyst composition is a metal-promoted, alumina- or silica-bound zeolite beta, and said second catalyst composition is ZSM-5 having incorporated therein an activity promoter selected from the group consisting of silicon, phosphorus, sulfur, and combinations thereof. According to the '051 patent, the use of the separate catalytic stages improves the conversion of $C_9+$ aromatic compounds and naphthalenes to xylenes and decreases the amount of undesirable ethylbenzene in the product.

Contrary to the teaching in U.S. Pat. No. 5,905,051, it has now been found that a single stage catalyst system comprising at least two different, specific molecular sieves exhibits enhanced activity for the removal of ethyl-group containing aromatic compounds in $C_9+$ aromatic feeds without overall reduction in the conversion of the $C_9+$ feed to useful compounds, such as xylenes.

SUMMARY

Accordingly the invention resides in a process for converting $C_9+$ aromatic hydrocarbons to lighter aromatic products, comprising the step of contacting a feed comprising $C_9+$ aromatic hydrocarbons under transalkylation reaction conditions with a catalyst composition comprising:

(i) a first molecular sieve selected from the group consisting of ZSM-12, mordenite and a porous crystalline inorganic oxide material having an X-ray diffraction pattern including d-spacing maxima at 12.4±0.25, 6.9±0.15, 3.57±0.07 and 3.42±0.07; and (ii) a second molecular sieve having a constraint index ranging from 3 to 12, wherein at least the first molecular sieve has a hydrogenation component associated therewith and wherein the first and second molecular sieves are contained in the same catalyst bed, the $C_9+$ aromatic hydrocarbons being converted under said transalkylation reaction conditions to a reaction product containing xylene.

In one embodiment, the first molecular sieve is ZSM-12 and the second molecular sieve is ZSM-5.

Conveniently, the catalyst composition is particulate and the first and second molecular sieves are contained in separate catalyst particles which are physically mixed in said catalyst bed.

Alternatively, the catalyst composition is particulate and the first and second molecular sieves are each contained in the same catalyst particles.

Typically, the feed also contains benzene or toluene.

In a further aspect the invention resides in a process for producing benzene comprising the steps of:

(a) reacting $C_9$ + aromatic hydrocarbons and toluene under transalkylation reaction conditions over a catalyst composition comprising:

(i) a first molecular sieve selected from the group consisting of ZSM-12, mordenite and a porous crystalline inorganic oxide material having an X-ray diffraction pattern including d-spacing maxima at 12.4±0.25, 6.9±0.15, 3.57±0.07 and 3.42±0.07; and (ii) a second molecular sieve having a constraint index ranging from 3 to 12, wherein at least the first molecular sieve has a hydrogenation component associated therewith and wherein the first and second molecular sieves are contained in the same catalyst bed, to produce a product stream comprising benzene and xylene; and (b) distilling the benzene from said product stream to obtain a benzene product.

DETAILED DESCRIPTION OF THE EMBODIMENTS

The present invention provides a process for converting a feed comprising C$_9$+ aromatic hydrocarbons, optionally together with added toluene or benzene, to produce a product containing benzene, toluene and xylenes. The process involves contacting the feed under transalkylation reaction conditions with a catalyst composition comprising at least two different molecular sieves which are contained in the same catalyst bed.

Catalyst Composition

The catalyst composition used in the process of the invention comprises:

(i) a first molecular sieve selected from the group consisting of ZSM-12, mordenite and a porous crystalline inorganic oxide material having an X-ray diffraction pattern including d-spacing maxima at 12.4±0.25, 6.9±0.15, 3.57±0.07 and 3.42±0.07; and (ii) a second molecular sieve having a constraint index ranging from 3 to 12.

With regard to the first molecular sieve, ZSM-12 is more particularly described in U.S. Pat. No. 3,832,449. Mordenite occurs naturally but may also be used in one of its synthetic forms, such as TEA-mordenite (i.e., synthetic mordenite prepared from a reaction mixture comprising a tetraethylammonium directing agent), which is disclosed in U.S. Pat. Nos. 3,766,093 and 3,894,104. Examples of suitable porous crystalline inorganic oxide materials having the defined X-ray diffraction pattern include MCM-22, PSH-3, SSZ-25, MCM-36, MCM-49 or MCM-56. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575 and MCM-56 is described in U.S. Pat. No. 5,362,697. The entire contents of each of the aforementioned patents are incorporated herein by reference.

With regard to the second molecular sieve, suitable materials having a constraint index of 3 to 12 include ZSM-5, ZSM-11, ZSM-22, ZSM-23, ZSM-35, ZSM-48, ZSM-57 and ZSM-58. ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

Typically, the second molecular sieve constitutes from 5 to 95 wt %, such as from in excess of 20 to 80 wt % based on the total weight of the first and second molecular sieves in the catalyst composition.

In one embodiment, the first molecular sieve is ZSM-12 and the second molecular sieve is ZSM-5.

Where the first molecular sieve is ZSM-12, the ZSM-12 can have a composition involving the molar relationship:

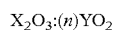

$$X_2O_3:(n)YO_2$$

wherein X is a trivalent element, such as aluminum, boron, iron, indium and/or gallium, preferably aluminum; Y is a tetravalent element, such as silicon, tin and/or germanium, preferably silicon; and n is less than 75, such as from 20 to less than 60. The ZSM-12 may further be selected so as to have an average crystal size of less than 0.1 micron, such as about 0.05 micron, and a Diffusion Parameter, $D/r^2$, for mesitylene of at least $1000 \times 10^{-6}$ sec$^{-1}$, such as at least $2000 \times 10^{-6}$ sec$^{-1}$, when measured at a temperature of 100° C. and a mesitylene pressure of 2 torr.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The ZSM-12 used as the first molecular sieve may also be arranged to have an Alpha value of at least 150, such as at least 300. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

ZSM-12 having the composition, crystal size, Diffusion Parameter and alpha value described in the preceding paragraphs can be produced by crystallization of a synthesis mixture containing sources of alkali or alkaline earth metal (M) cations, normally sodium, an oxide of a trivalent element (X), normally alumina, an oxide of a tetravalent element (Y), normally silica, methyltriethylammonium ions (R), normally present as the iodide salt, hydroxyl ions and water. The synthesis mixture may have a composition, expressed in terms of mole ratios of oxides, as follows:

| Component | Useful | Preferred |
|---|---|---|
| YO/XO | 20-100 | 40-80 |
| HO/YO | 10-100 | 15-40 |
| OH$^-$/YO | 0.1-0.6 | 0.15-0.4 |
| R/YO | 0.1-0.6 | 0.15-0.4 |
| M/YO | 0.1-0.6 | 0.15-0.4 |

The synthesis mixture may also contain nucleating seeds of ZSM-12 and, where such seeds are present, they typically constitute 0.05-5 wt % of the mixture. Crystallization of the synthesis mixture may be carried out under either stirred or static conditions, preferably stirred conditions, at a temperature of 160° C. or less, such as 140 to 160° C. for 48 to 500 hours, whereafter the resultant ZSM-12 crystals are separated from the mother liquor and recovered It may be desirable to incorporate each molecular sieve in the catalyst composition with another material that is resistant to the temperatures and other conditions employed in the transalkylation process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with the or each molecular sieve, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, e.g. bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the or each molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the or each molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

Each molecular sieve is usually admixed with the binder or matrix material so that the final catalyst composition contains the binder or matrix material in an amount ranging from 5 to 90 wt. %, and typically from 10 to 60 wt. %.

In the process of the invention, the first and second molecular sieves are contained in the same catalyst bed. Normally this is achieved either by physically mixing separate particles of the individual molecular sieves, preferably in bound form, or by co-extruding a mixture of the molecular sieves, typically with a binder, such that each particle of the final catalyst composition contains both the first and second molecular sieves. Alternatively, the particles of one of the first and second molecular sieves can be formed as a binder for the other of said first and second molecular sieves, such as is described in International Patent Publication No. WO 97/45198, the entire contents of which are incorporated herein by reference.

At least the first molecular sieve, and preferably each molecular sieve, in the catalyst composition has associated therewith at least one hydrogenation component, such as tungsten, vanadium, molybdenum, rhenium, chromium, manganese, a metal selected from Group VIII of the Periodic Table of the Elements (CAS version, 1979), or mixtures thereof. Specific examples of useful Group VIII metals are iron, ruthenium, osmium, nickel, cobalt, rhodium, iridium, and noble metals such as platinum or palladium. Preferably, the hydrogenation component is palladium, platinum or rhenium.

The amount of the hydrogenation component is selected according to a balance between hydrogenation activity and catalytic functionality. Less of the hydrogenation component is required when the most active metals such as platinum are used as compared to palladium, which does not possess such strong hydrogenation activity. Generally, the catalyst composition contains less than 10 wt % of the hydrogenation component and typically from 0.01 wt % to 2 wt % of said component.

The hydrogenation component can be incorporated into the catalyst composition by co-crystallization, exchanged into the composition to the extent a Group IIIA element, e.g., aluminum, is in the molecular sieve structure, impregnated therein, or mixed with the molecular sieve and binder. Such component can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)4Cl_2 \cdot H_2O$.

Alternatively, a compound of the hydrogenation component may be added to the molecular sieve when it is being composited with a binder, or after the molecular sieve and binder have been formed into particles by extrusion or pelletizing.

After treatment with the hydrogenation component, the molecular sieve is usually dried by heating at a temperature of 65° C. to 160° C. (150° to 320° F.), typically 110 to 143° C. (230° to 290° F.), for at least 1 minute and generally not longer than 24 hours, at pressures ranging from 100 to 200 kPa (0 to 15 psig). Thereafter, the molecular sieve may be calcined in a stream of dry gas, such as air or nitrogen, at temperatures of from 260° to 650° C. (500° to 1200° F.) for 1 to 20 hours. Calcination is typically conducted at pressures ranging from 100 to 300 kPa (0 to 30 psig).

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° to 650° C. (500° to 1200° F.) for at least one hour, specifically 1 to 20 hours, at a pressure of 100 to 2590 kPa (0 to 360 psig).

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320 to 480° C. (600 to 900° F.). The source of sulfur can be contacted with the catalyst via a carrier gas, such as hydrogen or nitrogen.

The Feed

The aromatic feed used in the process of the invention comprises one or more aromatic compounds containing at least 9 carbon atoms. Specific $C_9+$ aromatic compounds found in a typical feed include mesitylene(1,3,5-trimethylbenzene), durene(1,2,4,5-tetramethylbenzene), hemimellitene(1,2,4-trimethylbenzene), pseudocumene(1,2,4-trimethylbenzene), 1,2-methylethylbenzene, 1,3- methylethylbenzene, 1,4-methylethylbenzene, propyl-substituted benzenes, butyl-substituted benzenes, and dimethylethylbenzenes. Suitable sources of the $C_9+$ aromatics are any $C_9+$ fraction from any refinery process that is rich in aromatics. This aromatics fraction contains a substantial proportion of $C_9+$ aromatics, e.g., at least 80 wt % $C_9 +$ aromatics, wherein preferably at least 80 wt %, and more preferably more than 90 wt %, of the hydrocarbons will range from $C_9$ to $C_{12}$. Typical refinery fractions which may be useful include catalytic reformate, FCC naphtha or TCC naphtha.

The feed to the process of the invention may also includes benzene or toluene. Thus, in one practical embodiment, the feed to the transalkylation reactor comprises $C_9+$ aromatics hydrocarbons and toluene. The feed may also include recycled/unreacted toluene and $C_9+$ aromatics that is obtained by distillation of the effluent product of the transalkylation reaction itself. Typically, toluene constitutes from 40 to 90 wt. %, such as from 50 to 70 wt. % of the entire feed, whereas the $C_9+$ aromatics component constitutes from 10 to 60 wt. %, such as from 30 to 50 wt. % of the entire feed to the transalkylation reaction zone.

Hydrocarbon Conversion Process

The process can be conducted in any appropriate reactor including a radial flow, fixed bed, continuous down flow or fluid bed reactor. The transalkylation reaction conditions typically include a temperature ranging from about 343° to about 510° C. (650° to 950° F.), such as from about 400° to about 454° C. (750° to 850° F.); a pressure from about 380 to about 4240 kPa (50 to 600 psig), such as from about 1480 to about 3550 kPa (200 to 500 psig); a hydrogen to hydrocarbon molar ratio from about 1 to about 5, such as from about 1 to about 3 and a WHSV of about 0.2 to about 20, such as from 1 to about 5. The transalkylation reaction conditions are sufficient to convert the heavy aromatic feed to a product containing substantial quantities of $C_6$-$C_8$ aromatic compounds, such as benzene, toluene and xylenes, especially benzene and xylene.

The invention will now be more particularly described with reference to the following Examples.

EXAMPLE 1 (COMPARATIVE)

A two bed catalyst composition was prepared in which the first bed contained a rhenium-impregnated ZSM-12 catalyst (65 wt % ZSM-12/35 wt % alumina and 0.5 wt % rhenium) which was steamed in the final stage of catalyst preparation for 5.5 hours at 480° C. (900° F.) and the second bed contained a ZSM-5 catalyst (65 wt % ZSM-5/35 wt % alumina). The ZSM-12 used in the first bed had a silica/alumina molar ratio of about 200, an alpha value of 30, a crystal size of about 0.1 micron and a $D/r^2$ for mesitylene of $1900 \times 10^{-6}$ sec$^{-1}$ at a temperature of 100° C. and a mesitylene pressure of 2 torr. The ZSM-5 used in the second bed had a crystal size of 0.02 to 0.05 micron and a silica/alumina molar ratio equal to approximately 60. The weight ratio of first bed to second bed was 9:1.

EXAMPLE 2

A single bed catalyst composition was prepared by co-extruding a mixture of 40 wt % of the ZSM-12 used in Example 1, 40 wt % of the ZSM-5 used in Example 1 and 20 wt % alumina. The extrudate was converted to H-form by precalcining in nitrogen, exchanging with ammonium nitrate solution, then calcining in air for 6 hours at 540° C. (1000° F.).

The resultant catalyst particles were then impregnated with rhenium to a level of 0.5 wt % rhenium by weight over the overall catalyst composition and calcined in air for 1 hour at 524° C. (975° F.). This material was then steamed for 5.5 hours at 900° F., after which the catalyst had an alpha value of 67.

EXAMPLE 3

A single bed catalyst composition was prepared in the same way as Example 2 but with the ZSM-5 employed having crystal size of 0.2 to 0.5 micron and silica/alumina molar ratio equal to approximately 25.

EXAMPLE 4

The catalyst compositions of Examples 1 to 3 were used in separate runs to effect transalkylation of a mixture of 61 wt % toluene, 0.12 wt % ethylbenzene, 3.5 wt % xylenes, 0.36 wt % cumene, 1.15 wt % n-propylbenzene, 13.55 wt % ethyltoluenes, 19.36 wt % trimethylbenzenes, 0.35 wt % diethylbenzenes, 0.42 wt % dimethylethylbenzenes, and 0.21 wt % indane at a temperature of about 425° C., a pressure of 2445 kPa (340 psig), a hydrogen to hydrocarbon molar ratio of 1.02 and a WHSV of 6. The results are summarized in Table 1 below.

It will be seen from Table 1 that the co-extruded single bed catalysts of Examples 2 to 4 exhibited about twice the conversion activity for ethyl-containing $C_9+$ aromatic hydrocarbons than the two bed catalyst of Example 1. Moreover, the conversion of ethyl group-containing aromatics increased from about 41 wt % for the two-bed catalyst of Example 1 to 80-86 wt % for the coextruded single bed catalysts of Examples 2 and 3.

TABLE 1

|  | Example 1 | Example 2 | Example 3 |
|---|---|---|---|
| Temp (° C.) | 427 | 428 | 425 |
| Days on Stream | 1.5 | 2.5 | 1.5 |
| Wt %, H/C Basis |  |  |  |
| C1 | 0.13 | 0.05 | 0.15 |
| C2 | 0.47 | 0.97 | 0.95 |
| C3 | 0.43 | 0.26 | 0.27 |
| C4 | 0.12 | 0.07 | 0.04 |
| C5 | 0.01 | 0.01 | 0.01 |
| benzene | 10.43 | 10.07 | 9.50 |
| toluene | 35.92 | 42.72 | 44.11 |
| ethylbenzene | 2.31 | 0.62 | 0.67 |
| xylenes | 31.31 | 30.65 | 29.00 |
| ethyltoluenes | 4.30 | 1.28 | 1.64 |
| trimethylbenzenes | 10.70 | 11.66 | 11.87 |
| diethylbenzenes | 0.10 | 0.00 | 0.00 |
| dimethylethylbenzenes | 1.68 | 0.46 | 0.55 |
| tetramethylbenzenes | 0.74 | 0.51 | 0.55 |
| indan | 0.08 | 0.00 | 0.04 |
| naphthalene | 0.11 | 0.06 | 0.07 |
| methylnaphthalenes | 0.32 | 0.17 | 0.20 |
| other | 0.84 | 0.45 | 0.39 |
| Ethyl Conversion (wt %) | 41.43 | 83.95 | 80.59 |
| Propyl Conversion (wt %) | 100.00 | 100.00 | 100.00 |
| Toluene Conversion (wt %) | 41.12 | 29.97 | 27.70 |
| A9+ Conversion (wt %) | 46.94 | 59.46 | 57.10 |

EXAMPLE 5

A small crystal, high activity ZSM-12 was synthesized from a mixture comprising 11280 g of water, 1210 g of methyltriethylammonium chloride (MTEACl), 1950 g of Ultrasil PM, 229 g of sodium aluminate solution (45%), and 364 g of 50% sodium hydroxide solution. The mixture had the following molar composition:

| | |
|---|---|
| SiO/AlO = | 50 |
| HO/SiO = | 22 |
| OH⁻/SiO = | 0.2 |
| Na⁺/SiO = | 0.2 |
| MTEACl/SiO = | 0.26 |

The mixture was reacted at 320° F. (160° C.) in a 5-gal autoclave with stirring at 150 RPM for 144 hours. The product was filtered, washed with deionized (DI) water and dried at 250° F. (120° C.). The XRD pattern of the as-synthesized material showed the typical pure phase of ZSM-12 topology. The SEM of the as-synthesized material showed that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 44.98, an Alpha value of 500 and a $D/r^2$ for mesitylene of greater than $5000 \times 10^{-6}$ sec$^{-1}$ at a temperature of 100° C. and a mesitylene pressure of 2 torr.

A mixture containing 40 wt % of the ZSM-12 produced as above, 40 wt % ZSM-5, and 20 wt % alumina was extruded into pellets 1.3 mm (1/20 inch) in length and having a quadrulobe cross-section. The pellets were dried at 120° C. (250° F.) then calcined in nitrogen for 3 hours at 480° C. (900° F.). This material was then exchanged with ammonium nitrate, dried at 120° C. (250° F.) and then calcined in air for 6 hours at 540° C. (1000° F.). 0.1% Pd was then added to the catalyst by incipient wetness impregnation from an aqueous solution of tetraammine palladium nitrate. The impregnated material was dried at 120° C. (250° F.) then calcined in air for 6 hours at 350° C. (660° F.) to produce a final catalyst.

3 gm of the resultant catalyst composition was used to effect transalkylation of a mixture of toluene/C$_9$+ aromatic hydrocarbon mixture having the composition given in Table 2 at a temperature of about 480° C., a pressure of 2170 kPa (300 psig), a hydrogen to hydrocarbon molar ratio of 2 and a WHSV of 2.7. The results after 4.4 days on stream are summarized in Table 2 below.

TABLE 2

| Wt %, H/C Basis | Feed | Product |
|---|---|---|
| C− | | 8.24 |
| Non-Aromatics | | 0.04 |
| Benzene | | 12.79 |
| Toluene | 61.27 | 39.58 |
| Ethylbenzene | 0.03 | 0.11 |
| Xylenes | 0.26 | 28.80 |
| C | 29.82 | 8.45 |
| C | 8.31 | 0.86 |
| C+ | 0.30 | 1.12 |
| Total | 99.99 | 99.99 |
| Toluene Conversion (%) | | 35.39 |
| A Conversion (%) | | 71.64 |
| A Conversion (%) | | 89.46 |
| Ethyl Conversion (%) | | 96.52 |
| Propyl Conversion (%) | | 97.19 |

The results in Table 2 show that the catalyst of Example 5 was highly active, particularly for the conversion of the C$_9$ + aromatics, including the ethyl-containing materials. However, the particular catalyst tested did show evidence of aging as the run progressed.

We claim:

1. A process for converting C9+ aromatic hydrocarbons to lighter aromatic products, comprising the step of contacting a feed comprising C9+ aromatic hydrocarbons under transalkylation reaction conditions with a coextruded catalyst composition comprising the molecular sieves ZSM-12 and ZSM-5
   wherein at least ZSM-12 has a hydrogenation component associated therewith, said hydrogenation component selected from rhenium, palladium, and mixtures thereof, the C9+ aromatic hydrocarbons being converted under said transalkylation reaction conditions to a reaction product containing xylene.

2. The process of claim 1, wherein ZSM-5 constitutes from 5 wt % to 95 wt % based on the total weight of the molecular sieves.

3. The process of claim 1, wherein ZSM-5 constitutes from in excess of 20 to 80 wt % based on the total weight of the molecular sieves.

4. The process of claim 1, wherein the hydrogenation component is rhenium.

5. The process of claim 1, wherein the hydrogenation component is sulfided prior to said contacting step.

6. The process of claim 1, wherein the feed also contains benzene or toluene.

7. The process of claim 1, wherein the transalkylation reaction conditions comprise a temperature of about 343° C. to about 510° C., a pressure of about 446 to about 4240 kPa-a, a hydrogen to hydrocarbon mole ratio of about 1 to about 5 and a WHSV of about 0.2 to about 20.

8. The process of claim 1, wherein the transalkylation reaction conditions comprise a temperature of about 400° C. to about 454° C.; a pressure of about 1480 to about 3550 kPa-a; a hydrogen to hydrocarbon molar ratio of about 1 to about 3; and a WHSV of about 1 to about 5.

9. A process for producing benzene comprising the steps of:
   (a) reacting C9+ aromatic hydrocarbons and toluene under transalkylation reaction conditions over a coextruded catalyst composition comprising the molecular sieves ZSM-12 and ZSM-5
   wherein at least ZSM-12 has a hydrogenation component associated therewith, said hydrogenation component selected from rhenium, palladium, and mixtures thereof to produce a product stream comprising benzene and xylene; and
   (b) distilling the benzene from said product stream to obtain a benzene product.

* * * * *